United States Patent
Vidal

(10) Patent No.: US 7,351,406 B2
(45) Date of Patent: Apr. 1, 2008

(54) COMPOSITIONS FOR BODY HAIRS AND/OR HEAD HAIR

(75) Inventor: Richard Vidal, Orleans (FR)

(73) Assignee: Merck Chimie SAS (FR)

( * ) Notice: Subject to any disclaimer, the term of this patent is extended or adjusted under 35 U.S.C. 154(b) by 360 days.

(21) Appl. No.: 10/940,334

(22) Filed: Sep. 14, 2004

(65) Prior Publication Data

US 2006/0051382 A1    Mar. 9, 2006

(30) Foreign Application Priority Data

Sep. 7, 2004    (FR) .................................. 04 09440

(51) Int. Cl.
*A61K 9/00*    (2006.01)
*A61K 9/14*    (2006.01)

(52) U.S. Cl. ..................... 424/70.7; 424/489

(58) Field of Classification Search ............... 424/489, 424/70.7
See application file for complete search history.

(56) References Cited

U.S. PATENT DOCUMENTS 4,339,337 A * 7/1982 Tricot et al. ............. 252/62.54
6,327,779 B1 * 12/2001 Skipper ........................ 30/74
6,463,661 B2   10/2002 Skipper
2001/0022025 A1   9/2001 Skipper

FOREIGN PATENT DOCUMENTS

| EP | 0 038 730 A1 | 10/1981 |
| EP | 0 628 304 A1 | 12/1994 |
| EP | 1 249 228 A1 | 10/2002 |
| FR | 2 825 247 A1 | 12/2002 |

* cited by examiner

*Primary Examiner*—Johann R. Richter
*Assistant Examiner*—Konata M George
(74) *Attorney, Agent, or Firm*—Lerner, David, Littenberg, Krumholz & Mentlik, LLP

(57) ABSTRACT

Compositions which can be applied to body hairs or head hair, comprising an aqueous suspension of magnetic latex microspheres and of colloidal nanoparticles of magnetic pigment.

4 Claims, 4 Drawing Sheets

COMPOSITIONS FOR BODY HAIRS AND/OR HEAD HAIR

The invention relates to compositions which can be applied to body hairs or head hair. Specifically, the invention relates to a mascara, a shaving composition (foam, gel, cream, etc.) or a hair composition (lotion, shampoo, etc.).

Mascara is a very popular type of make-up for women who wish to thicken or accentuate their eyelashes and the user is always looking for mascaras which give considerable curling of the eyelashes.

Thus, the mascara should allow an optimum length and should give the eyelashes a suitable colour, thickness and curling.

It is commonplace to use, in mascaras, a variable proportion according to the nature of the formulation of film-forming substances which make it possible to confer good stability on said compositions.

At the current time, the film-forming polymers used do not always make it possible to obtain satisfactory curling of the eyelashes. In addition, some film-forming polymers form, on the eyelashes after drying, a whitish film resulting in make-up which is not aesthetically pleasing.

Thus, Patent EP 0 628 304 describes a cosmetic composition containing a pseudolatex which has good properties of persistence, i.e. it is difficult to remove from the support by means of simple washing with water for example.

A need therefore still exists for a mascara which has good curling properties and which makes it possible to form an invisible make-up.

The cutting or removal of body hair is typically part of daily life. Whether for cosmetic reasons (shaving the face, the legs, etc.) or for functional reasons (preparing a patient for an operation), there is a need for a comfortable, effective and relatively inexpensive method.

The method most commonly used for cutting or removing body hair employs a razor, which may or may not be electric, which often results in irritation of the skin or cuts. Although shaving foams are used to reduce the phenomenon of irritation during contact of the blade with the skin, the body hair being cut simply at the level of the skin, the shaving must be carried out daily in order to minimize regrowth of the body hair, which, despite everything, induces irritation in sensitive individuals. The use of an electric razor has the same disadvantages, whereas the use of wax, while it avoids daily use, is often very painful.

Thus, a need still exists for a shaving foam which allows effective and less painful shaving.

U.S. Pat. No. 6,463,661 describes a method of shaving using a razor equipped with a blade coupled to a magnet and comprising the application, before shaving, of a solution containing magnetic particles to the body hairs, so as to cover them with said magnetic particles, and the use of the razor such that the magnet applies its magnetic force onto said magnetic particles, thus causing the body hairs to stand up so as to facilitate the shaving. The magnetic particles used are metal particles, in particular based on $Fe_3O_4$ obtained from a sand. However, these particles are used directly with no purification, and no precise formulation is described.

The aim of the present invention is therefore to propose compositions which can be applied to body hairs or head hair in order to make them stand up. In the case of the mascara composition, the composition has good eyelash-curling properties and provides a uniform application which gives the eyelashes a natural appearance.

Consequently, a subject of the present invention is compositions which can be applied to body hairs or head hair, comprising an aqueous suspension of magnetic latex microspheres and of colloidal nanoparticles of magnetic pigment.

In a preferred embodiment of the invention, the composition which can be applied to body hairs or head hair is a mascara, a shaving composition or a hair composition comprising an aqueous suspension of magnetic latex microspheres and of colloidal nanoparticles of magnetic pigment.

The term "mascara" is understood to mean the basic elements for the formulation of mascara, in particular a mascara comprising a cosmetically acceptable medium, i.e. a medium compatible with keratin materials.

For the purpose of the present invention, the term "magnetic latex" is understood to mean latices such as those described in European Patent EP 0 038 730 and American Patent U.S. Pat. No. 4,339,337, and the expression "colloidal nanoparticles of magnetic pigment" is understood to mean nanoparticles consisting of a mixture of $Fe_3O_4$ oxide coated with an ionic or nonionic surfactant, such as those described in European Patent EP 0 038 730 and American Patent U.S. Pat. No. 4,339,337.

In a preferred embodiment of the invention, the magnetic latex represents from 5 to 20% of the total weight of the composition and the magnetic pigment represents 15 to 30% by weight of the composition.

In another preferred embodiment of the invention, the diameter of the magnetic latex microspheres is between 100 nanometres and 2 micrometres, preferably between 700 and 1.3 micrometres, and the diameter of the colloidal nanoparticles of magnetic pigment is between 2 and 50 nanometres, preferably between 5 and 20 nanometres.

The hair lotions and the shaving formulations, to which the magnetic latex microspheres and the colloidal nanoparticles of magnetic pigment are added, can be any type of solutions of compositions known to those skilled in the art, such as creams, gels, foams and lotions.

The mascara compositions according to the invention can also be any mascara compositions known to those skilled in the art.

They can contain antistatic compounds. By way of example of antistatics, mention may be made of anionic, nonionic, cationic or amphoteric surfactants, polysaccharides such as chitin or its derivatives, or chitosan and its derivatives.

The mascara compositions according to the invention can also contain film-forming agents which confer good resistance on the mascara. Among the cosmetically acceptable film-forming agents, mention may be made, for example, of polymers such as acrylic polymers, polyethylene-based polymers, copolymers of polyvinyl pyrrolidone, ethylene vinyl acetates, dimethicone gum and resins, such as silicone resins.

They can optionally contain other usual additives, for example antioxidants. Among the suitable antioxidants, mention may be made of propylparaben, butylparaben or mixtures thereof.

The mascaras can also contain one or more pigment(s) suitable for use around the eyes. As examples of pigments, mention may be made of metal oxides, bismuth oxychloride and chromium oxide. Viscosity-modifying agents such as waxes and other gelling agents, along with fillers such as nylon, albumin, talc and other fillers typically used in these compositions, may also be added.

The mascaras according to the invention may be provided in the form of an aqueous gel, or of a wax/water, water/wax, oil/water and water/oil dispersion.

Those skilled in the art will take care to choose these optional additional compounds and/or the amounts thereof, such that the advantageous properties of the composition according to the invention are not impaired by the addition envisaged.

The compositions according to the invention can be prepared according to the usual methods in the fields under consideration.

A subject of the invention is also a device for the conditioning and application of a mascara illustrated in FIGS. 1 to 3 and comprising a container (1) containing said mascara (M) to be applied and an applicator (2). The applicator (2) comprises a stem (3) equipped at one end with a gripping member (4) which constitutes the cap for closing the container (1) and, at the other end, a brush (5) consisting of fibres intended for application of the mascara.

Incorporated within the gripping member (4), the length of which is preferably approximately ⅔ of that of the container (1), is a stem which can be opened out (6), the end of which consists of a short-haired brush (7) capable of inducing a magnetic field between 0.7 and 1.5 tesla.

In another embodiment of the device illustrated in FIG. 3, the gripping member (7) can itself be a magnet.

The shaving compositions according to the invention can be used with any shaving device comprising a magnet close to the blade, such as that described in U.S. Pat. Nos. 6,327,779, 2001/0022025 and U.S. Pat. No. 6,463,661.

The effect of the presence of the magnetic latex and of the magnetic nanoparticles in the shaving compositions, when they are applied to the body hair, allow the body hair to stand up above the skin and to obtain a better shave, while at the same time decreasing the abrasive contact of the blade with the skin.

The magnetic field can be created by means of a ferric magnet, for example a neodyme/iron/boron, or samarium/cobalt magnet.

The invention also relates to the use of a composition according to the invention, for making body hairs stand up.

More particularly, the invention relates to the use of a mascara containing an aqueous suspension of magnetic latex microspheres, for curling the eyelashes.

A subject of the invention is also the use of an aqueous suspension of magnetic latex microspheres and of colloidal nanoparticles of magnetic pigment in a mascara composition comprising a cosmetically acceptable medium, for curling the eyelashes.

A subject of the invention is also a method for coating the eyelashes, comprising the application onto the eyelashes of a mascara composition as defined above.

In a preferred embodiment of the invention, the method for coating the eyelashes is carried out with an applicator element as described above.

The coating of the eyelashes is in particular a make-up method for cosmetic, not therapeutic, treatment of the eyelashes.

The mascara composition according to the invention is easily used by the consumer. It is simply applied to the upper or lower eyelashes and dries in 1 or 2 minutes. The eyelashes are long and well-separated and have a natural appearance.

The magnetic compositions applied to the body hairs or head hair, in particular to the eyelashes, makes them magnetizable and therefore makes it possible, when they are subjected to magnetic fields, to orient them in a desired direction. The magnetic force applied to the magnetic mascara also provides the energy required to overcome the reaction energy barriers and thus to result in a product being obtained which is stable on the eyelashes, maintaining them in the direction of the magnetic field for several hours after its action.

The example and the figures which follow illustrate the invention in greater detail:

EXAMPLE

Mascara Formulation

Figure 1:
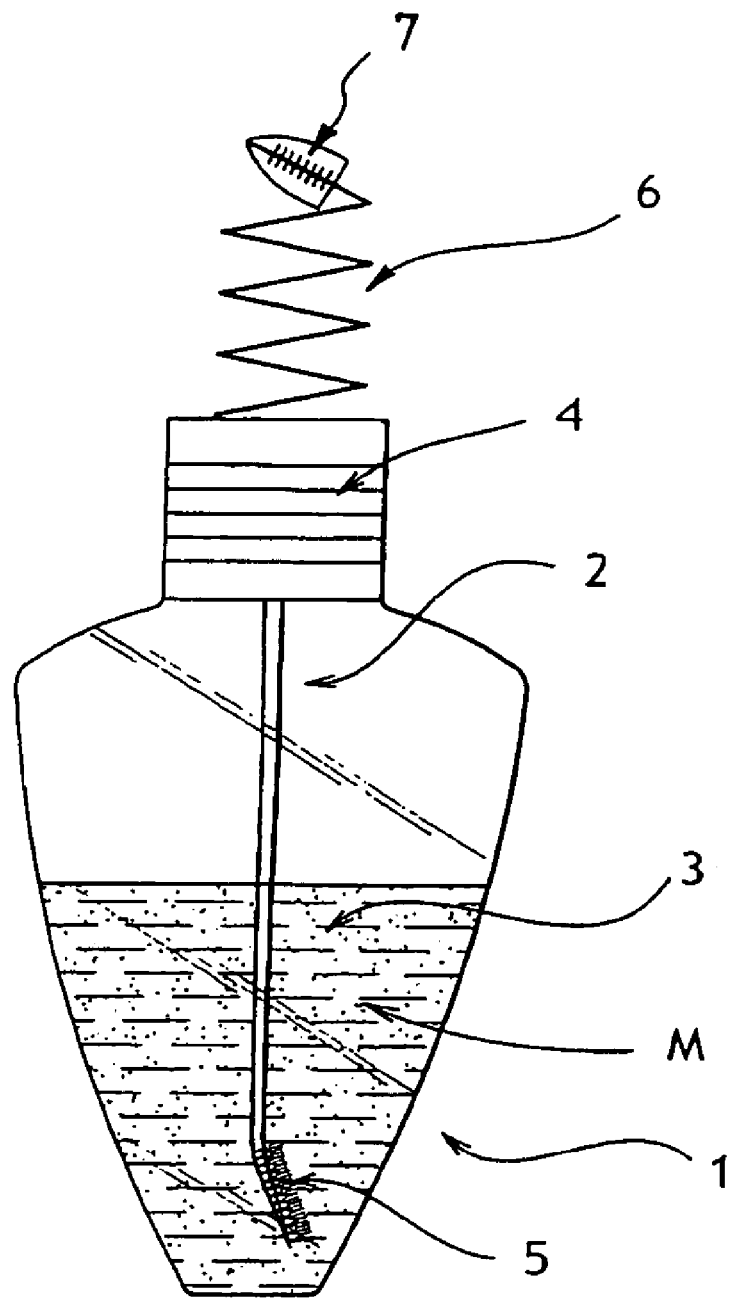
FIG. 1 represents a ready-to-use device for the conditioning and application of mascara according to the invention.
Figure 2:
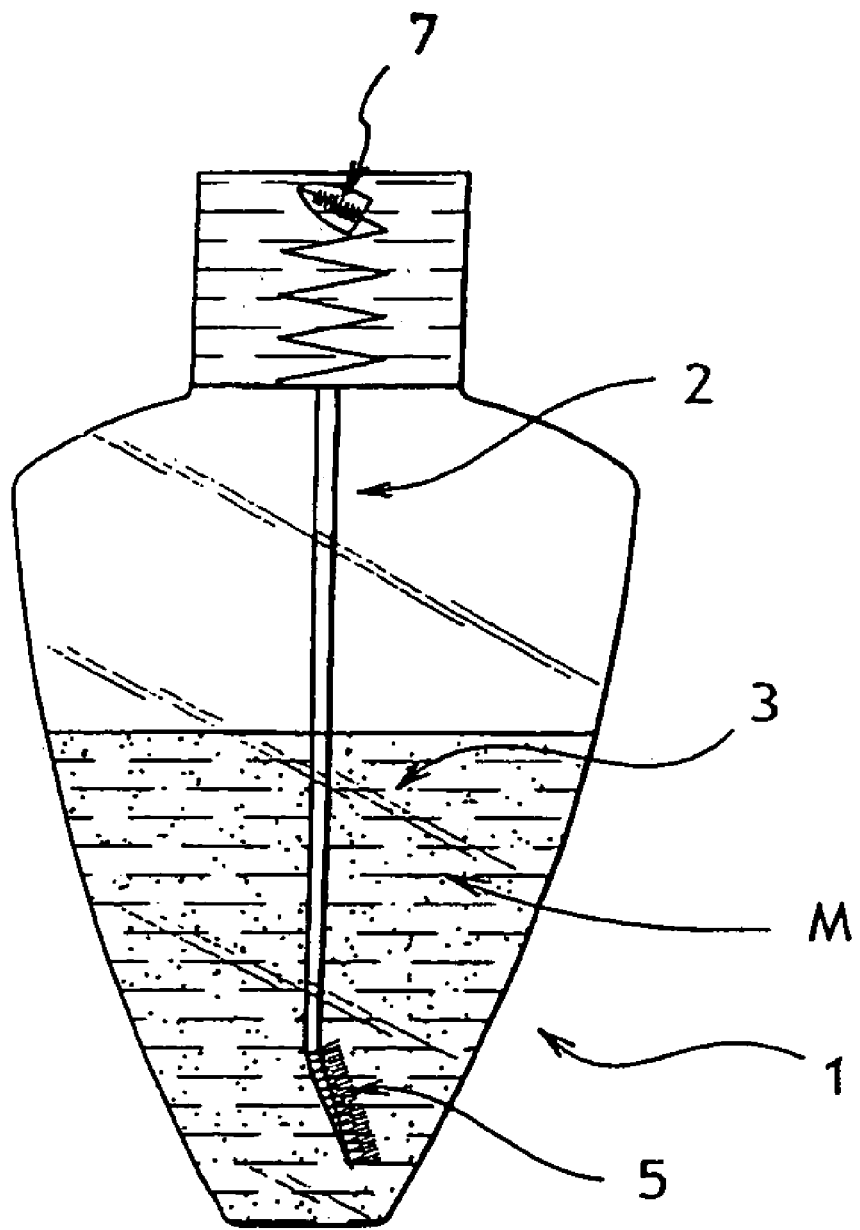
FIG. 2 illustrates a device for the conditioning and application of the mascara according to the invention in the conditioning state.
Figure 3:
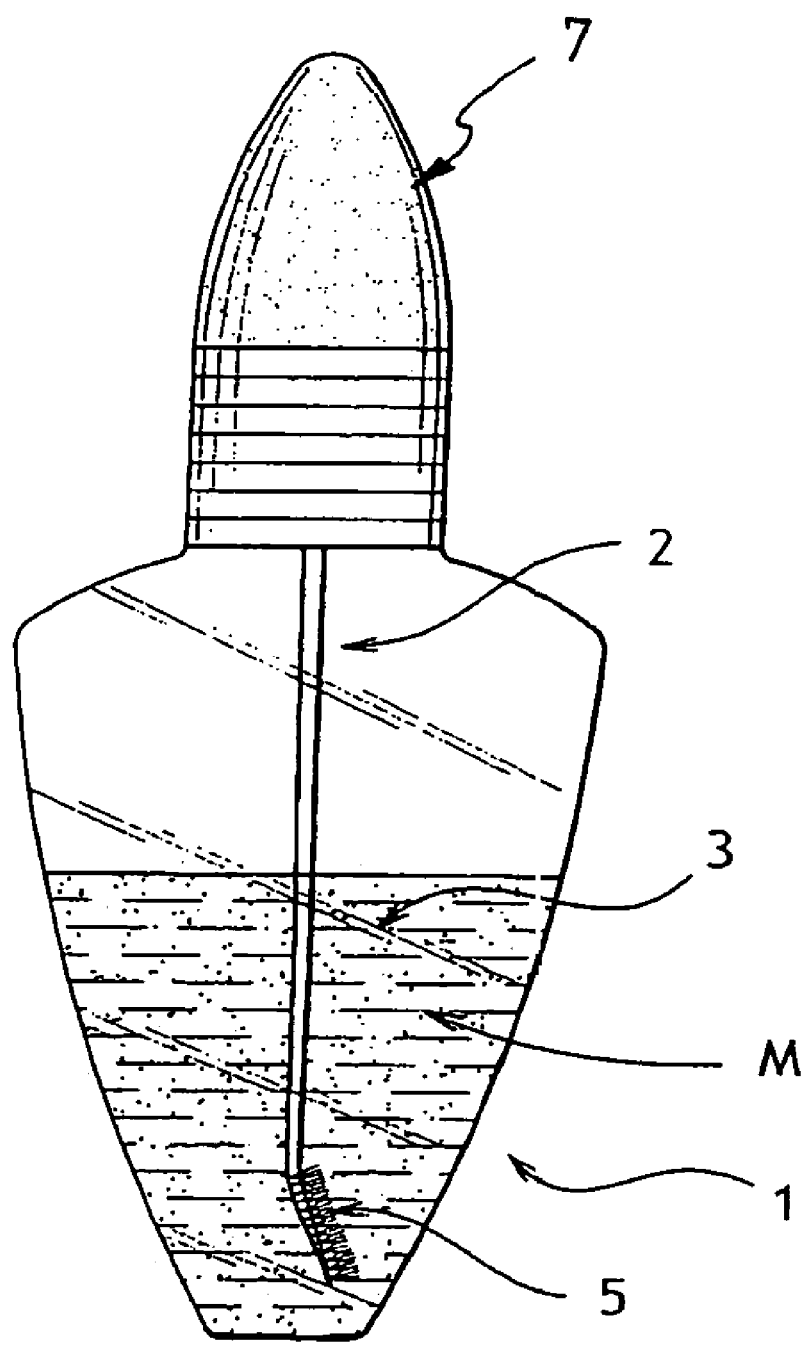
FIGS. 3 and 4 illustrate a device in which the gripping member is itself a magnet.
Figure 4:
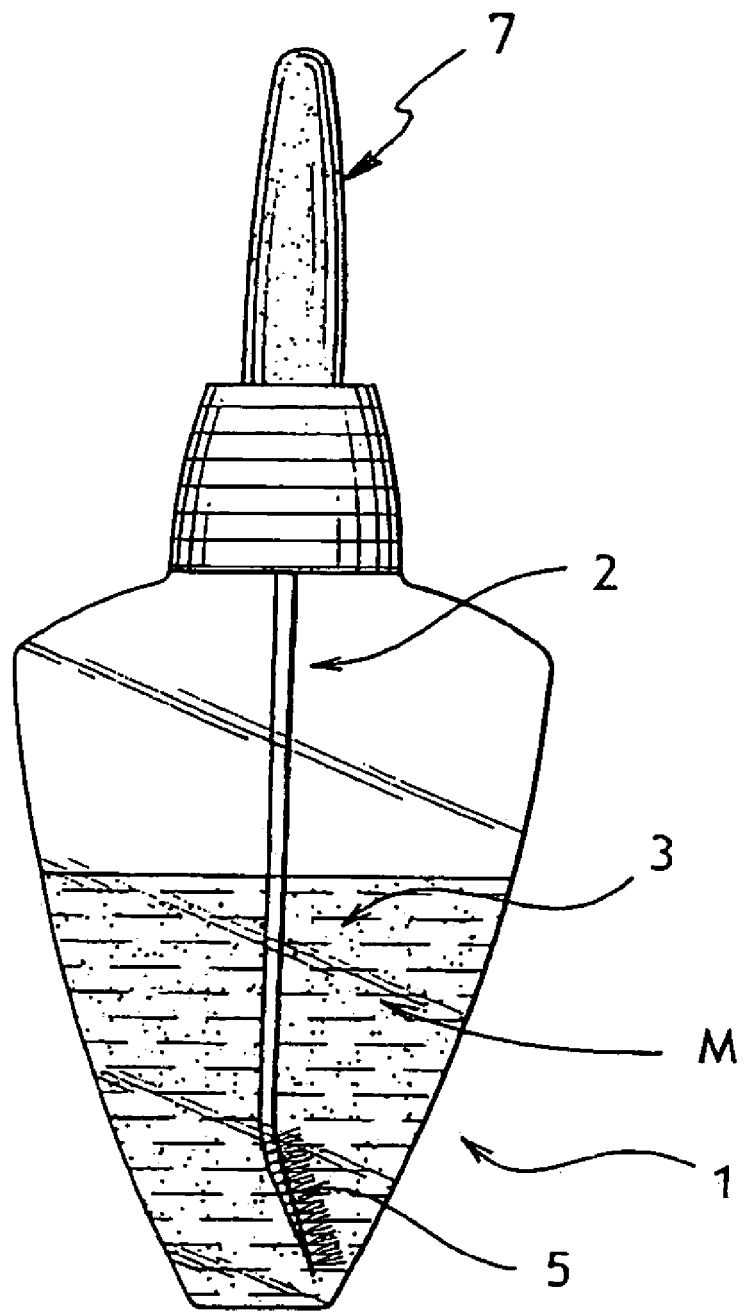

It is prepared according to techniques known to those skilled in the art, by mixing water-soluble film-forming polymers and polymeric nanospheres in dispersion in water.

| | |
|---|---|
| Copolymers of vinyl acetate and of vinylpyrrolidone | 23% |
| Water | 30% |
| Silicone oil | 5% |
| Triethanolamine | 2% |
| Magnetic latex microspheres | 5-20% |
| Magnetic pigment nanoparticles | 15-30% |

The invention claimed is:

1. A device for the conditioning and application of a mascara comprising a container containing said mascara to be applied, said mascara comprising an aqueous suspension of magnetic latex microspheres and of colloidal nanoparticles of magnetic pigment, and an applicator, said applicator having a stem including a first end comprising a gripping member/cap for closing the container, and a second end comprising a brush for the application of the mascara, wherein said gripping member/cap comprises a second stem having a first end, said second stem being extendable away from said gripping member/cap, wherein said first end of said second stem comprises a short haired brush capable of inducing a magnetic field between 0.7 and 1.5 tesla.

2. A method for making head hairs stand up comprising the step of applying to head hairs a composition comprising an aqueous suspension of magnetic latex microspheres and of colloidal nanoparticles of magnetic pigment.

3. A method of curling the eyelashes comprising the step of applying to the eyelashes a mascara composition comprising a cosmetically acceptable medium and an aqueous suspension of magnetic latex microspheres and of colloidal nanoparticles of magnetic pigment.

4. A method for coating the eyelashes comprising the step of applying onto the eyelashes a mascara composition wherein said mascara comprises an aqueous suspension of magnetic latex microspheres and of colloidal nanoparticles of magnetic pigment.

* * * * *